(12) United States Patent
Young et al.

(10) Patent No.: US 7,189,825 B2
(45) Date of Patent: *Mar. 13, 2007

(54) CANCEROUS DISEASE MODIFYING ANTIBODIES

(75) Inventors: David S. F. Young, Toronto (CA); Susan E. Hahn, Toronto (CA); Helen P. Findlay, Toronto (CA)

(73) Assignee: Arius Research Inc., Ontario (CA)

( * ) Notice: Subject to any disclaimer, the term of this patent is extended or adjusted under 35 U.S.C. 154(b) by 37 days.

This patent is subject to a terminal disclaimer.

(21) Appl. No.: 10/892,597

(22) Filed: Jul. 15, 2004

(65) Prior Publication Data

US 2004/0253653 A1    Dec. 16, 2004

Related U.S. Application Data

(62) Division of application No. 10/348,231, filed on Jan. 21, 2003, now Pat. No. 7,009,040.

(51) Int. Cl.
*C07K 16/00* (2006.01)
*C12P 21/08* (2006.01)
*G01N 33/574* (2006.01)
*A61K 39/395* (2006.01)
*C12P 21/04* (2006.01)

(52) U.S. Cl. .............................. 530/388.1; 530/387.3; 530/388.8; 530/391.3; 530/391.7; 424/133.1; 424/141.1; 424/155.1; 424/183.1; 435/7.23; 435/69.6; 435/70.21

(58) Field of Classification Search ............. 530/387.1, 530/387.3, 388.1, 388.8, 391.7, 391.3; 424/130.1, 424/133.1, 155.1, 181.1, 183.1, 141.1; 435/69.6, 435/70.21, 7.23
See application file for complete search history.

(56) References Cited

U.S. PATENT DOCUMENTS

| | | |
|---|---|---|
| 4,861,581 A | 8/1989 | Epstein et al. |
| 5,171,665 A | 12/1992 | Hellstrom et al. |
| 5,484,596 A | 1/1996 | Hanna, Jr. et al. |
| 5,693,763 A | 12/1997 | Codington et al. |
| 5,750,102 A | 5/1998 | Eisenbach et al. |
| 5,780,033 A | 7/1998 | Torchilin et al. |
| 5,783,186 A | 7/1998 | Arakawa et al. |
| 5,849,876 A | 12/1998 | Linsley et al. |
| 5,869,045 A | 2/1999 | Hellstrom et al. |
| 5,869,268 A | 2/1999 | Kudo et al. |

OTHER PUBLICATIONS

Campbell et al. Biology, 5th ed. p. 856, 1999.*
Co et al. Nature, 351(6):501-502, Jun. 6, 1991.*
Presta et al. Biochemical Society Transactions, 30(4):487-490, 2002.*

T. Karpanen et al, "Vascular endothelial growth factor C promotes tumor lymphangiogenesis and intralymphatic tumor growth", Cancer Research, 61:1786-1790 (Mar. 2001).

W. Waud et al, "Characterization of in vivo mammary and prostate tumor xenograft models for growth and response to clinical anticancer agents", Contrib Oncol Basel Karger, 54:305-315 (1999).

G. Klement et al, "Differences in therapeutic indexes of combination metronomic chemotherapy and an anti-VEGFR-2 antibody in multidrug-resistant human breast cancer xenografts", Clinical Cancer Research, 8:221-232 (Jan. 2002).

D. Blakey et al, "Antitumor activity of the novel vascular targeting agent ZD6126 in a panel of tumor models", Clinical Cancer Research, 8:1974-1983 (Jun. 2002).

Z. Xiao et al, "Generation of a baculovirus recombinant prostate-specific membrane antigen and its use in the development of a novel protein biochip quantitative immunoassay", Protein Expresion and Purification, 19:12-21 (2000).

S. Gulchard et al, "Schedule-dependent activity of topotecan in OVCAR-3 ovarian carcinoma xenograft: pharmacokinetic and pharmacodynamic evaluation", Clinical Cancer Research, 7:3222-3228 (Oct. 2001).

V. Von Gruenigen et al, "Efficacy of intraperitoneal adenovirus-mediated p53 gene therapy in ovarian cancer", Int. J. Gynecol. Cancer, 9:365-372 (1999).

N. Guilbaud et al, "Marked antitumor activity of a new potent acronycine derivative in orthotopic models of human solid tumors", Clinical Cancer Research, 7:2573-2580 (Aug. 2001).

K. Olson et al, "Inhibition of prostate carcinoma establishment and metastatic growth in mice by an antiangiogenin monoclonal antibody", Int. J. Cancer, 98:923-929 (2002).

S. Hirschfeld et al, "Oncology drug development: United States Food and Drug Administration perspective", Critical Reviews in Oncology/Hematology, 42:137-143 (2002).

P. Therasse et al, "New guidelines to evaluate the response to treatment in solid tumors", Journal of the National Cancer Institute, 92(3):205-216 (Feb. 2000).

G. Eckhardt et al, "Developmental therapeutics: successes and failures of clinical trial designs of targeted compounds", in American Society of Clinical Oncology, pp. 209-219 (2003).

(Continued)

*Primary Examiner*—David J. Blanchard
(74) *Attorney, Agent, or Firm*—McHale & Slavin, P.A.

(57) ABSTRACT

The present invention relates to a method for producing patient cancerous disease modifying antibodies using a novel paradigm of screening. By segregating the anti-cancer antibodies using cancer cell cytotoxicity as an end point, the process makes possible the production of anti-cancer antibodies for therapeutic and diagnostic purposes. The antibodies can be used in aid of staging and diagnosis of a cancer, and can be used to treat primary tumors and tumor metastases. The anti-cancer antibodies can be conjugated to toxins, enzymes, radioactive compounds, and hematogenous cells.

16 Claims, 6 Drawing Sheets

OTHER PUBLICATIONS

P. Smith et al, "Anti-interleukin-6 monoclonal antibody Induces regression of human prostate cancer xenografts in nude mice", The Prostate, 48:47-53 (2001).

M. Chatterjee et al, "Idiotypic antibody immunotherapy of cancer", Cancer Immunol Immunother, 38:75-82 (1994).

R. Jain, "Barriers to drug delivery in solid tumors", Scientific American, 271(1):58-65 (Jul. 1994).

L. Presta et al, "Engineering therapeutic antibodies for improved function", Biochemical Society Transactions, 30(4):487-490 (2002).

S. Shak, "Overview of the trastuzumab (Herceptin) anti-HER2 monoclonal antibody clinical program in HER2-overexpressing metastatic breast cancer", Seminars in Oncology, 26(4 Suppl 12):71-77 (Aug. 1999).

S. Seaver, "Monoclonal antibodies in industry: more difficult than originally thought", Genetic Engineering News, 14(14):pp. 10 and 21 (1994).

L. Weiner, "An overview of monoclonal antibody therapy of cancer", Seminars in Oncology, 26(4 Suppl 12):41-50 (Aug. 1999).

* cited by examiner

Survival Curve

CANCEROUS DISEASE MODIFYING ANTIBODIES

REFERENCE TO RELATED APPLICATION

This application is a divisional of application Ser. No. 10/348,231, filed on Jan. 21, 2003, now U.S. Pat. No. 7,009,040, issued on Mar. 7, 2006, the contents of which are herein incorporated by reference. filed on Jan. 21, 2003, the contents of which are herein incorporated by reference.

FIELD OF THE INVENTION

This invention relates to the isolation and production of cancerous disease modifying antibodies (CDMAB) and to the use of these CDMAB in therapeutic and diagnostic processes, optionally in combination with one or more chemotherapeutic agents. The invention further relates to binding assays which utilize the CDMABs of the instant invention.

BACKGROUND OF THE INVENTION

Each individual who presents with cancer is unique and has a cancer that is as different from other cancers as that person's identity. Despite this, current therapy treats all patients with the same type of cancer, at the same stage, in the same way. At least 30% of these patients will fail the first line therapy, thus leading to further rounds of treatment and the increased probability of treatment failure, metastases, and ultimately, death. A superior approach to treatment would be the customization of therapy for the particular individual. The only current therapy which lends itself to customization is surgery. Chemotherapy and radiation treatment can not be tailored to the patient, and surgery by itself, in most cases is inadequate for producing cures.

With the advent of monoclonal antibodies, the possibility of developing methods for customized therapy became more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be designed to specifically target transformed cells by binding specifically to these cancer antigens; thus giving rise to the belief that monoclonal antibodies can serve as "Magic Bullets" to eliminate cancer cells. Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. Such a course of therapy would, ideally, increase the rate of cures, and produce better outcomes, thereby satisfying a long-felt need.

Historically, the use of polyclonal antibodies has been used with limited success in the treatment of human cancers. Lymphomas and leukemias have been treated with human plasma, but there were few prolonged remission or responses. Furthermore, there was a lack of reproducibility and there was no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least four clinical trials for human breast cancer which produced only one responder from at least 47 patients using antibodies against specific antigens or based on tissue selectivity. It was not until 1998 that there was a successful clinical trial using a humanized anti-her 2 antibody in combination with Cisplatin. In this trial 37 patients were accessed for responses of which about a quarter had a partial response rate and another half had minor or stable disease progression.

The clinical trials investigating colorectal cancer involve antibodies against both glycoprotein and glycolipid targets. Antibodies such as 17-1A, which has some specificity for adenocarcinomas, had undergone Phase 2 clinical trials in over 60 patients with only one patient having a partial response. In other trials, use of 17-1A produced only one complete response and two minor responses among 52 patients in protocols using additional cyclophosphamide. Other trials involving 17-1A yielded results that were similar. The use of a humanized murine monoclonal antibody initially approved for imaging also did not produce tumor regression. To date there has not been an antibody that has been effective for colorectal cancer. Likewise there have been equally poor results for lung cancer, brain cancers, ovarian cancers, pancreatic cancer, prostate cancer, and stomach cancer. There has been some limited success in the use of anti-GD3 monoclonal antibody for melanoma. Thus, it can be seen that despite successful small animal studies that are a prerequisite for human clinical trials, the antibodies that have been tested have been for the most part ineffective.

Prior Patents

U.S. Pat. No. 5,750,102 discloses a process wherein cells from a patient's tumor are transfected with MHC genes which may be cloned from cells or tissue from the patient. These transfected cells are then used to vaccinate the patient.

U.S. Pat. No. 4,861,581 discloses a process comprising the steps of obtaining monoclonal antibodies that are specific to an internal cellular component of neoplastic and normal cells of the mammal but not to external components, labeling the monoclonal antibody, contacting the labeled antibody with tissue of a mammal that has received therapy to kill neoplastic cells, and determining the effectiveness of therapy by measuring the binding of the labeled antibody to the internal cellular component of the degenerating neoplastic cells. In preparing antibodies directed to human intracellular antigens, the patentee recognizes that malignant cells represent a convenient source of such antigens.

U.S. Pat. No. 5,171,665 provides a novel antibody and method for its production. Specifically, the patent teaches formation of a monoclonal antibody which has the property of binding strongly to a protein antigen associated with human tumors, e.g. those of the colon and lung, while binding to normal cells to a much lesser degree.

U.S. Pat. No. 5,484,596 provides a method of cancer therapy comprising surgically removing tumor tissue from a human cancer patient, treating the tumor tissue to obtain tumor cells, irradiating the tumor cells to be viable but non-tumorigenic, and using these cells to prepare a vaccine for the patient capable of inhibiting recurrence of the primary tumor while simultaneously inhibiting metastases. The patent teaches the development of monoclonal antibodies which are reactive with surface antigens of tumor cells. As set forth at col. 4, lines 45 et seq., the patentees utilize autochthonous tumor cells in the development of monoclonal antibodies expressing active specific immunotherapy in human neoplasia.

U.S. Pat. No. 5,693,763 teaches a glycoprotein antigen characteristic of human carcinomas and not dependent upon the epithelial tissue of origin.

U.S. Pat. No. 5,783,186 is drawn to Anti-Her2 antibodies which induce apoptosis in Her2 expressing cells, hybridoma cell lines producing the antibodies, methods of treating cancer using the antibodies and pharmaceutical compositions including said antibodies.

U.S. Pat. No. 5,849,876 describes new hybridoma cell lines for the production of monoclonal antibodies to mucin antigens purified from tumor and non-tumor tissue sources.

U.S. Pat. No. 5,869,268 is drawn to a method for generating a human lymphocyte producing an antibody specific to a desired antigen, a method for producing a monoclonal antibody, as well as monoclonal antibodies produced by the method. The patent is particularly drawn to the production of an anti-HD human monoclonal antibody useful for the diagnosis and treatment of cancers.

U.S. Pat. No. 5,869,045 relates to antibodies, antibody fragments, antibody conjugates and single chain immunotoxins reactive with human carcinoma cells. The mechanism by which these antibodies function is two-fold, in that the molecules are reactive with cell membrane antigens present on the surface of human carcinomas, and further in that the antibodies have the ability to internalize within the carcinoma cells, subsequent to binding, making them especially useful for forming antibody-drug and antibody-toxin conjugates. In their unmodified form the antibodies also manifest cytotoxic properties at specific concentrations.

U.S. Pat. No. 5,780,033 discloses the use of autoantibodies for tumor therapy and prophylaxis. However, this antibody is an antinuclear autoantibody from an aged mammal. In this case, the autoantibody is said to be one type of natural antibody found in the immune system. Because the autoantibody comes from "an aged mammal", there is no requirement that the autoantibody actually comes from the patient being treated. In addition the patent discloses natural and monoclonal antinuclear autoantibody from an aged mammal, and a hybridoma cell line producing a monoclonal antinuclear autoantibody.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies which are useful in treating a cancerous disease.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies, and a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

In addition to anti-cancer antibodies, the patient can elect to receive the currently recommended therapies as part of a multi-modal regimen of treatment. The fact that the antibodies isolated via the present methodology are relatively non-toxic to non-cancerous cells allows for combinations of antibodies at high doses to be used, either alone, or in conjunction with conventional therapy. The high therapeutic index will also permit re-treatment on a short time scale that should decrease the likelihood of emergence of treatment resistant cells.

Furthermore, it is within the purview of this invention to conjugate standard chemotherapeutic modalities, e.g. radionuclides, with the CDMABs of the instant invention, thereby focusing the use of said chemotherapeutics.

If the patient is refractory to the initial course of therapy or metastases develop, the process of generating specific antibodies to the tumor can be repeated for re-treatment. Furthermore, the anti-cancer antibodies can be conjugated to red blood cells obtained from that patient and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibody conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody dependent cellular cytotoxicity or complement dependent cytotoxicity. For example murine IgM and IgG2a antibodies can activate human complement by binding the C-1 component of the complement system thereby activating the classical pathway of complement activation which can lead to tumor lysis. For human antibodies the most effective complement activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody mediated cancer cell killing which are more widely accepted. The first is the use of antibodies as a vaccine to induce the body to produce an immune response against the putative cancer antigen that resides on the tumor cell. The second is the use of antibodies to target growth receptors and interfere with their function or to down regulate that receptor so that effectively its function is lost.

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach cancerous disease modifying antibodies and antigen binding fragments thereof.

It is a further objective of the instant invention to produce cancerous disease modifying antibodies whose cytotoxicity is mediated through antibody dependent cellular toxicity.

It is yet an additional objective of the instant invention to produce cancerous disease modifying antibodies whose cytotoxicity is mediated through complement dependent cellular toxicity.

It is still a further objective of the instant invention to produce cancerous disease modifying antibodies whose cytotoxicity is a function of their ability to catalyze hydrolysis of cellular chemical bonds.

A still further objective of the instant invention is to produce cancerous disease modifying antibodies which are useful for in a binding assay for diagnosis, prognosis, and monitoring of cancer.

Other objects and advantages of this invention will become apparent from the following description wherein are set forth, by way of illustration and example, certain embodiments of this invention.

DETAILED DESCRIPTION OF THE INVENTION

EXAMPLE 1

Figure 1:
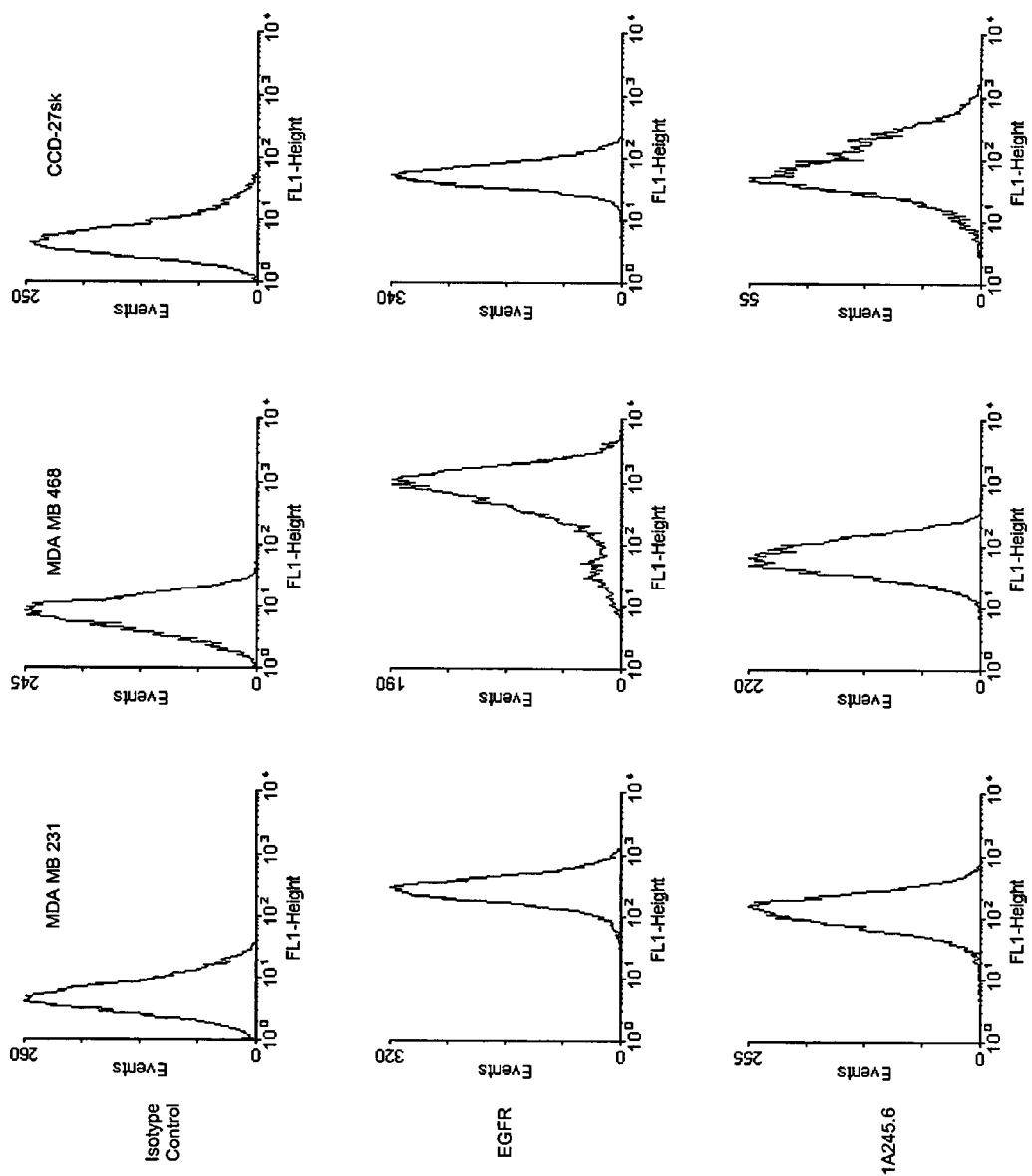
FIG. 1 includes representative FACS histograms of 1A245.6 antibodies, isotype control antibodies for both antibodies, anti-EGFR antibodies directed against several cancer cell lines and non-cancer cells.

Hybridomas Production—Hybridoma Cell Line 7BD-33-11A, 1A245.6, 11BD-2E11-2 Hybridomas:

The hybridoma cell lines 7BD-33-11A and 1A245.6 were deposited, in accordance with the Budapest Treaty, with the American Type Culture Collection, 10801 University Blvd., Manassas, Va. 20110-2209 on Jan. 8, 2003, under Accession Number PTA-4890 and PTA-4889, respectively. In accordance with 37 CFR 1.808, the depositors assure that all restrictions imposed on the availability to the public of the deposited materials will be irrevocably removed upon the granting of a patent.

The hybridoma cell line 11BD-2E11-2 was deposited, in accordance with the Budapest Treaty, with the American Type Culture Collection, 10801 University Blvd., Manassas, Va. 20110-2209 on Nov. 11, 2003, under Accession Number PTA-5643. In accordance with 37 CFR 1.808, the depositors assure that all restrictions imposed on the availability to the public of the deposited materials will be irrevocably removed upon the granting of a patent.

To produce the hybridoma that produce the anti-cancer antibody 7BD-33-11A single cell suspensions of the antigen, i.e. human breast cancer cells, were prepared in cold PBS. Eight to nine weeks old BALB/c mice were immunized by injecting 100 microliters of the antigen-adjuvant containing between 0.2 million and 2.5 million cells in divided doses both subcutaneously and intraperitoneally with Freund's Complete Adjuvant. Freshly prepared antigen-adjuvant was used to boost the immunized mice at between 0.2 million and 2.5 million cells in the same fashion three weeks after the initial immunization, and two weeks after the last boost. A spleen was used for fusion at least two days after the last immunization. The hybridomas were prepared by fusing the isolated splenocytes with Sp2/0 myeloma partners. The supernatants from the fusions were tested for subcloning of the hybridomas.

To produce the hybridoma that produce the anti-cancer antibody 1A245.6 single cell suspensions of the antigen, i.e. human breast cancer cells, were prepared in cold PBS. Eight to nine weeks old BALB/c mice were immunized by injecting 100 microliters of the antigen-adjuvant containing 2.5 million cells in divided doses both subcutaneously and intraperitoneally with Freund's Complete Adjuvant. Freshly prepared antigen-adjuvant was used to boost the immunized mice at 2.5 million cells in the same fashion three weeks after the initial immunization, two weeks later, five weeks later and three weeks after the last boost. A spleen was used for fusion at least three days after the last immunization. The hybridomas were prepared by fusing the isolated splenocytes with NSO-1 myeloma partners. The supernatants from the fusions were tested for subcloning of the hybridomas.

To produce the hybridoma that produce the anti-cancer antibody 11BD-2E11-2 single cell suspensions of the antigen, i.e. human breast cancer cells, were prepared in cold PBS. Eight to nine weeks old BALB/c mice were immunized by injecting 100 microliters of the antigen-adjuvant containing between 0.2 million and 2.5 million cells in divided doses both subcutaneously and intraperitoneally with Freund's Complete Adjuvant. Freshly prepared antigen-adjuvant was used to boost the immunized mice at between 0.2 million and 2.5 million cells in the same fashion two to three weeks after the initial immunization, and two weeks after the last boost. A spleen was used for fusion at least two days after the last immunization. The hybridomas were prepared by fusing the isolated splenocytes with NSO-1 myeloma partners. The supernatants from the fusions were tested for subcloning of the hybridomas.

To determine whether the antibodies secreted by hybridoma cells are of the IgG or IgM isotype, an ELISA assay was employed. 100 microliters/well of goat anti-mouse IgG+IgM(H+L) at a concentration of 2.4 micrograms/mL in coating buffer (0.1M carbonate/bicarbonate buffer, pH 9.2–9.6) at 4° C. was added to the ELISA plates overnight. The plates were washed thrice in washing buffer (PBS+0.05% Tween). 100 microliters/well blocking buffer (5% milk in wash buffer) was added to the plate for 1 hr. at room temperature and then washed thrice in washing buffer. 100 microliters/well of hybridoma supernatant was added and the plate incubated for 1 hr. at room temperature. The plates were washed thrice with washing buffer and 1/5000 dilution of either goat anti-mouse IgG or IgM horseradish peroxidase conjugate (diluted in PBS containing 1% bovine serum albumin), 100 microliters/well, was added. After incubating the plate for 1 hr. at room temperature the plate was washed thrice with washing buffer. 100 microliters/well of TMB solution was incubated for 1–3 minutes at room temperature. The color reaction was terminated by adding 100 microliters/well 2M $H_2SO_4$ and the plate was read at 450 nm with a Perkin-Elmer HTS7000 plate reader. As indicated in Table 1 the 7BD-33-11A, 1A245.6, 11BD-2E11-2 hybridomas secreted primarily antibodies of the IgG isotype.

After one to four rounds of limiting dilution hybridoma supernatants were tested for antibodies that bound to target cells in a cell ELISA assay. Three breast cancer cell lines were tested: MDA-MB-231 (also referred to as MB-231), MDA-MB-468 (also referred to as MB-468), and SKBR-3. The plated cells were fixed prior to use. The plates were washed thrice with PBS containing $MgCl_2$ and $CaCl_2$ at room temperature. 100 microliters of 2% paraformaldehyde diluted in PBS was added to each well for ten minutes at room temperature and then discarded. The plates were again washed with PBS containing $MgCl_2$ and $CaCl_2$ three times at room temperature. Blocking was done with 100 microliters/well of 5% milk in wash buffer (PBS+0.05% Tween) for 1 hr at room temperature. The plates were washed thrice with wash buffer and the hybridoma supernatant was added at 100 microliters/well for 1 hr at room temperature. The plates were washed three times with wash buffer and 100 microliters/well of 1/5000 dilution of goat anti-mouse IgG or IgM antibody conjugated to horseradish peroxidase (diluted in PBS containing 1% bovine serum albumin) was added. After a one hour incubation at room temperature the plates were washed three times with wash buffer and 100 microliter/well of TMB substrate was incubated for 1–3 minutes at room temperature. The reaction was terminated with 100 microliters/well 2M $H_2SO_4$ and the plate read at 450 nm with a Perkin-Elmer HTS7000 plate reader. The results as tabulated in Table 1 were expressed as the number of folds above background compared to the IgG isotype control (3BD-27). The antibodies from the 7BD-33-11A and 1A245.6 hybridoma cell lines bound strongly to all 3 breast lines, with binding at least 6 times greater than background. Both antibodies bound most strongly to the MDA-MB-231 cell line. The antibodies from the 11BD-2E11-2 hybridoma cell line also bound most strongly to the MDA-MB-231 cell line, but did not demonstrate binding on the other 2 cell lines greater than background. These results suggest that the epitope recognized by this antibody is not present on MDA-MB-468 or SKBR-3 cells, and is distinct from the epitopes recognized by 7BD-33-11A and 1A245.6.

In conjunction with testing for antibody binding the cytotoxic effect of the hybridoma supernatants were tested in the same breast cancer cell lines: MDA-MB-231, MDA-MB-468 and SKBR-3. The Live/Dead cytotoxicity assay was obtained from Molecular Probes (Eu,OR). The assays were performed according to the manufacturer's instructions with the changes outlined below. Cells were plated before the assay at the predetermined appropriate density. After 2 days, 100 microliters of supernatant from the hybridoma microtitre plates were transferred to the cell plates and incubated in a 5% $CO_2$ incubator for 5 days. The wells that served as the positive controls were aspirated until empty and 100 microliters of sodium azide and/or cycloheximide was added. 3BD-27 monoclonal antibody was also added as an isotype control since it was known not to bind to the three breast cancer cell lines being tested. An anti-EGFR antibody (C225) was also used in the assay for comparison. After 5 days of treatment, the plate was then emptied by inverting and blotted dry. Room temperature DPBS containing $MgCl_2$ and $CaCl_2$ was dispensed into each well from a multichannel squeeze bottle, tapped three times, emptied by inversion and then blotted dry. 50 microliters of the fluorescent Live/Dead dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel. The results were tabulated in Table 1.

Differential cytotoxicity was observed with the 3 antibodies. 11BD-2E11-2 demonstrated killing of 39–73%, with the highest cytotoxicity observed in SKBR-3 cells. 1A245.6 and 7BD-33-11A demonstrated similar cytotoxicity in MDA-MB-231 cells, but 1A245.6 was also cytotoxic to MDA-MB-468 cells, while 7BD-33-11A was not.

This indicated the antibody derived form the hybridoma cell can produce cytotoxicity in cancer cells. There was also a general association between the degree of antibody binding and the cytotoxicity produced by the hybridoma supernatants. There were several exceptions to this trend such as the amount of cytotoxicity produced by 11BD-2E11-2 in MB-468 cancer cells, and SKBR-3 cancers despite a paucity of binding. This suggested that the antibody has a mediating action that was not detected by the cell ELISA binding assay in this cell type, or the assay did not detect the binding, which may be due to the constraints of the assay such as cell fixation. Finally, there existed yet another possibility, that is, the assay was not sensitive enough to detect the binding that was sufficient to mediate cytotoxicity in this particular situation. The other exception was the relative paucity of cytotoxicity of 7BD-33-11A towards MB-468 cells despite a 6 fold increase in binding over the background in comparison to an isotype control. This pointed to the possibility that binding was not necessarily predictive of the outcome of antibody ligation of its cognate antigen. The known non-specific cytotoxic agents cycloheximide produced cytotoxicity as expected.

TABLE 1

| Clone | Cytotoxicity (%) | | | | | | Binding (above bkgd) | | |
|---|---|---|---|---|---|---|---|---|---|
| | MB-231 | | MB-468 | | SKBR-3 | | MB-231 | MB-468 | SKBR-3 |
| | Average | CV | Average | CV | Average | CV | Fold | Fold | Fold |
| 1A245.6 | 17 | 7 | 13 | 5 | 44 | 8 | 23 | 10 | 16 |
| 7BD-33-11A | 16 | 2 | 2 | 2 | 29 | 3 | 13 | 6 | 9 |
| 11BD-2E11-2 | 39 | 2 | 66 | 1 | 73 | 18 | 11 | 2 | 1 |
| Cycloheximide | 49 | 9 | 24 | 5 | 56 | 14 | | | |

EXAMPLE 2

Antibody Production

Monoclonal antibodies were produced by culturing the hybridomas, 7BD-33-11A, 1A245.6, 11BD-2E11-2, in CL-1000 flasks (BD Biosciences, Oakville, ON) with collections and reseeding occurring twice/week and standard antibody purification procedures with Protein G Sepharose 4 Fast Flow (Amersham Biosciences, Baie d'Urfé, QC). It is within the scope of this invention to utilize monoclonal antibodies which are humanized, chimerized or murine antibodies. 7BD-33-11A, 1A245.6, 11BD-2E11-2 were compared to a number of both positive (anti-Fas (EOS9.1, IgM, kappa, 20 micrograms/mL, eBioscience, San Diego, Calif.), anti-Her2/neu (IgG1, kappa, 10 microgram/mL, Inter Medico, Markham, ON), anti-EGFR(C225, IgG1, kappa, 5 microgram/mL, Cedarlane, Hornby, ON), Cycloheximide (100 micromolar, Sigma, Oakville, ON), $NaN_3$ (0.1%, Sigma, Oakville, ON)) and negative (107.3 (anti-TNP, IgG1, kappa, 20 microgram/mL, BD Biosciences, Oakville, ON), G155–178 (anti-TNP, IgG2a, kappa, 20 microgram/mL, BD Biosciences, Oakville, ON), MPC-11 (antigenic specificity unknown, IgG2b, kappa, 20 microgram/mL), J606 (anti-fructosan, IgG3, kappa, 20 microgram/mL), IgG Buffer (2%)) controls in a cytotoxicity assay (Table 2). Breast cancer (MB-231, MB-468, MCF-7), colon cancer (HT-29, SW1116, SW620), lung cancer (NCI H460), ovarian cancer (OVCAR), prostate cancer (PC-3), and non-cancer (CCD 27sk, Hs888 Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, 100 microliters of purified antibody was diluted into media, and then were transferred to the cell plates and incubated in a 8% $CO_2$ incubator for 5 days. The plate was then emptied by inverting and blotted dry. Room temperature DPBS containing $MgCl_2$ and $CaCl_2$ was dispensed into each well from a multichannel squeeze bottle, tapped three times, emptied by inversion and then blotted dry. 50 microliters of the fluorescent Live/Dead dye diluted in DPBS containing $MgCl_2$ and $CaCl_2$ was added to each well and incubated at 37° C. in a 5% $CO_2$ incubator for 30 minutes. The plates were read in a Perkin-Elmer HTS7000 fluorescence plate reader and the data was analyzed in Microsoft Excel and the results were tabulated in Table 2. The data represented an average of four experiments tested in triplicate and presented qualitatively in the following fashion: 4/4 experiments greater than threshold cytotoxicity (+++), 3/4 experiments greater than threshold cytotoxicity (++), 2/4 experiments greater than threshold cytotoxicity (+). Unmarked cells in Table 2 represented inconsistent or effects less than the threshold cytotoxicity. The 7BD-33-11A and 1A245.6 antibodies demonstrated cytotoxicity in breast and prostate tumor cell lines selectively, while having no effect on non-transformed normal cells. Both demonstrated a 25–50% greater killing than the positive control anti-Fas antibody. 11BD-2E11-2 was specifically cytotoxic in breast and ovarian cancer cells, and did not affect normal cells. The chemical cytotoxic agents induced their expected cytotoxicity while a number of other antibodies which were

TABLE 2

| | | BREAST | | | COLON | | | LUNG | OVARY | PROSTATE | николас NORMAL | |
|---|---|---|---|---|---|---|---|---|---|---|---|---|
| | | MB-231 | MB-468 | MCF-7 | HT-29 | SW1116 | SW620 | NCI H460 | OVCAR | PC-3 | CCD 27sk | Hs888 Lu |
| | 11BD2E11-2 | – | – | + | – | – | – | – | + | – | – | – |
| | 7BD-33-11A | – | – | + | – | – | – | – | – | ++ | – | – |
| | 1A245.6 | – | – | + | – | – | – | – | – | ++ | – | – |
| Positive | anti-Fas | – | – | +++ | – | – | – | – | +++ | + | – | + |
| Controls | anti-Her2 | + | – | + | – | – | – | – | + | – | – | – |
| | anti-EGFR | – | +++ | + | – | +++ | – | – | + | – | + | – |
| | CHX (100 μM) | +++ | +++ | +++ | +++ | +++ | +++ | +++ | +++ | +++ | +++ | +++ |
| | $NaN_3$ (0.1%) | +++ | +++ | +++ | +++ | – | – | +++ | +++ | +++ | – | – |
| Negative | IgG1 | | | | | | | | +++ | | + | | |
| Controls | IgG2a | | | +++ | | + | | | | | | |
| | IgG2b | | | +++ | | | | | | | | |
| | IgG3 | | | | | | | | | | | |
| | IgG Buffer | + | | | | | | | | | | | cancer (CCD 27sk, Hs888 Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate included for comparison also performed as expected given the limitations of biological cell assays. In toto, it was shown that the three antibodies have cytotoxic activity against a number of cancer cell types. The antibodies were selective in their activity since not all cancer cell types were susceptible. Furthermore, the antibodies demonstrated functional specificity since they did not produce cytotoxicity against non-cancer cell types, which is an important factor in a therapeutic situation.

Cells were prepared for FACS by initially washing the cell monolayer with DPBS (without $Ca^{++}$ and $Mg^{++}$). Cell dissociation buffer (INVITROGEN) was then used to dislodge the cells from their cell culture plates at 37° C. After centrifugation and collection the cells were resuspended in Dulbecco's phosphate buffered saline containing $MgCl_2$, $CaCl_2$ and 25% fetal bovine serum at 4° C. (wash media) and counted, aliquoted to appropriate cell density, spun down to pellet the cells and resuspended in staining media (DPBS containing $MgCl_2$ and $CaCl_2$) containing 7BD-33-11A, 1A245.6, 11BD-2E11-2 or control antibodies (isotype control or anti-EGF-R) at 20 micrograms/mL on ice for 30 minutes. Prior to the addition of Alexa Fluor 488-conjugated secondary antibody the cells were washed once with wash media. The Alexa Fluor 488-conjugated antibody in staining media was then added for 20 minutes. The cells were then washed for the final time and resuspended in staining media containing 1 microgram/mL of propidium iodide. Flow cytometric acquisition of the cells was assessed by running samples on a FACScan using the CELLQUEST™ software (BD Biosciences). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform peak with a median fluorescent intensity of approximately 1–5 units. Live cells were acquired by gating for FSC and propidium iodide exclusion. For each sample, approximately 10,000 live cells were acquired for analysis and the results presented in Table 3. Table 3 tabulated the mean fluorescence intensity fold increase above isotype control and is presented qualitatively as: less than 5(−); 5 to 50 (+); 50 to 100 (++); above 100 (+++) and in parenthesis, the percentage of cells stained.

the context of antibody ligation in different cells was determinative of cytoxicity rather than just antibody binding.

EXAMPLE 3

Figure 5:
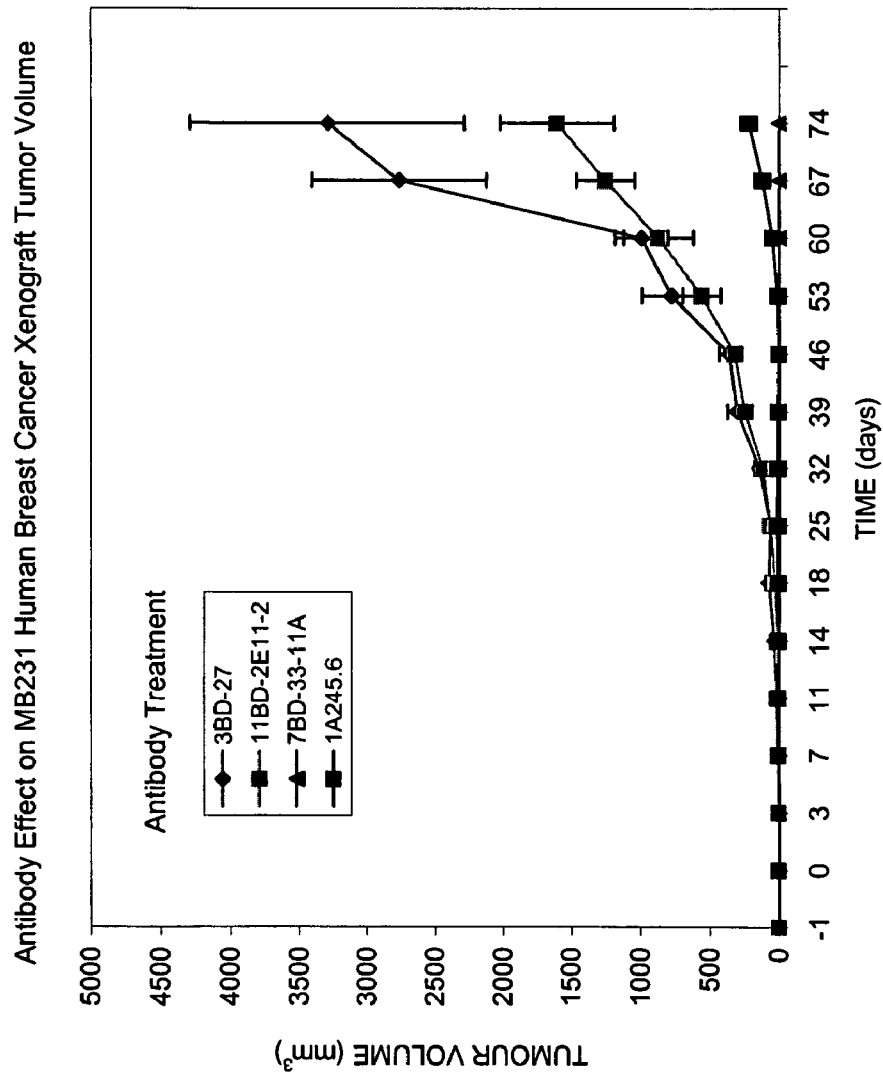
FIG. 5 is a graphical analysis of antibody effect on MB231 Human Breast Cancer tumor volume over time.
Figure 6:
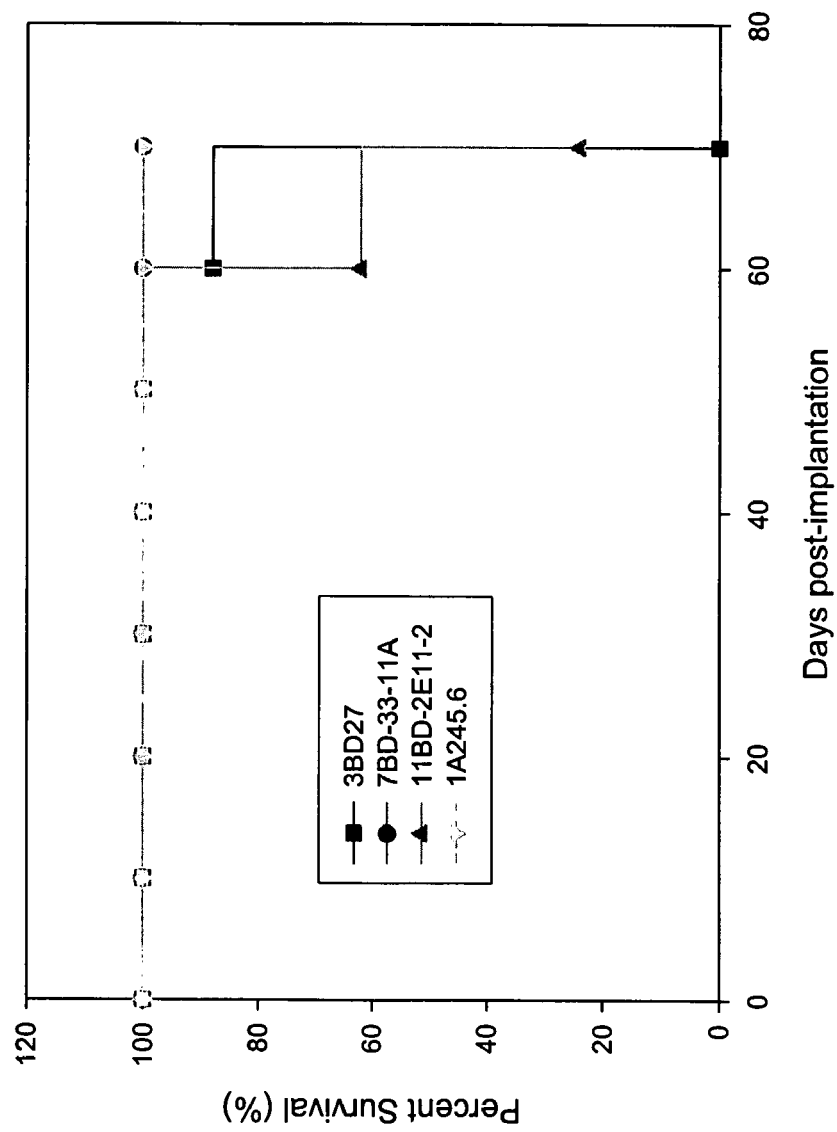
FIG. 6 is a graphical analysis quantifying percent survival over time relative to antibody therapy.

In Vivo Experiments:

Now with reference to the data shown in FIGS. 5 and 6, four to eight week old, female SCID mice were implanted with 5 million MDA-MB-231 human breast cancer cells in one hundred microliters injected subcutaneously in the scruff of the neck. The mice were randomly divided into four treatment groups of ten. On the day prior to implantation 20 mg/kg of either 11BD2E-11-2, 7BD-33-11A, 1A245.6 test antibodies or 3BD-27 isotype control antibody (known not to bind MDA-MB-231 cells) were administered intrapertioneally at a volume of 300 microliters after dilution from the stock concentration with a diluent that contained 2.7 mM KCl, 1 mM $KH_2PO_4$, 137 mM NaCl, 20 mM $Na_2HPO_4$. The antibodies were then administered once per week for a period of 7 weeks in the same fashion.

Tumor growth was measured about every seventh day with calipers for up to ten weeks or until individual animals reached the Canadian Council for Animal Care (CCAC) end-points. Body weights of the animals were recorded for the duration of the study. At the end of the study all animals were euthanised according to CCAC guidelines. There were no clinical signs of toxicity throughout the study. Body weight measured at weekly intervals was a surrogate for well-being and failure to thrive. There was a minimal difference in weight for the groups treated with the isotype control, 3BD-27, and 7BD-33-11A, 1A245.6, or 11BD-2E11-2. At day 60 (11 days after the cessation of treatment) tumor volume of the group treated with 1 A245.6 was 5.2% of the control group (p=0.0002) and demonstrated effectiveness at reducing tumor burden with antibody treatment. Those mice bearing cancer treated with 7BD-33-11A antibody were disease free and had no tumor burden. The tumor volume was lower in the 11BD-2E11-2 treatment group

TABLE 3

| Antibody | Isotype | BREAST | | | COLON | | | LUNG |
| --- | --- | --- | --- | --- | --- | --- | --- | --- |
| | | MB-231 | MB-468 | MCF-7 | HT-29 | SW116 | SW620 | NCI H460 |
| 11BD2E11-2 | IgG1, k | +(61%) | — | — | — | — | — | — |
| 7BD-33-11A | IgG2a, k | +(95%) | — | +(76%) | +(97%) | +(34%) | +(bimodal, 76%) | +(bimodal, 60%) |
| 1A245.6 | IgG1, k | +(98%) | +(78%) | +(74%) | ++ | +(23%) | +(bimodal, 71%) | +(bimodal, 70%) |
| anti-EGFR | IgG1, k | ++ | ++bimodal | — | +(97%) | +(43%) | — | +(bimodal, 80%) |
| anti-FAS | IgM, k | — | — | — | +(30%) | — | — | +(61%) |

Figure 2:
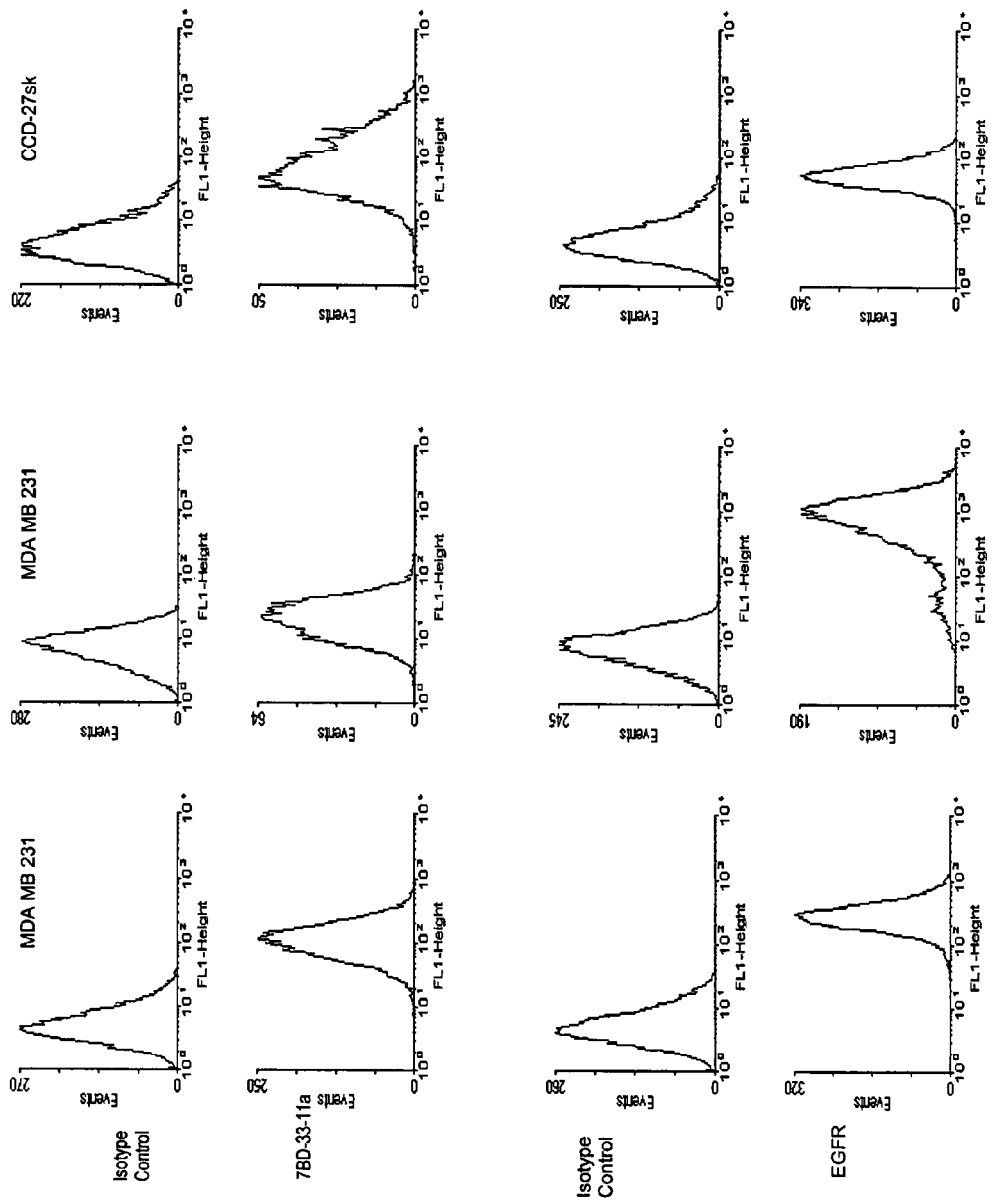
FIG. 2 includes representative FACS histograms of 7BD-33-11A antibodies, isotype control antibodies for 1A245.6, anti-EGFR antibodies, isotype control antibodies for anti-EGFR directed against several cancer cell lines and non-cancer cells.
Figure 3:
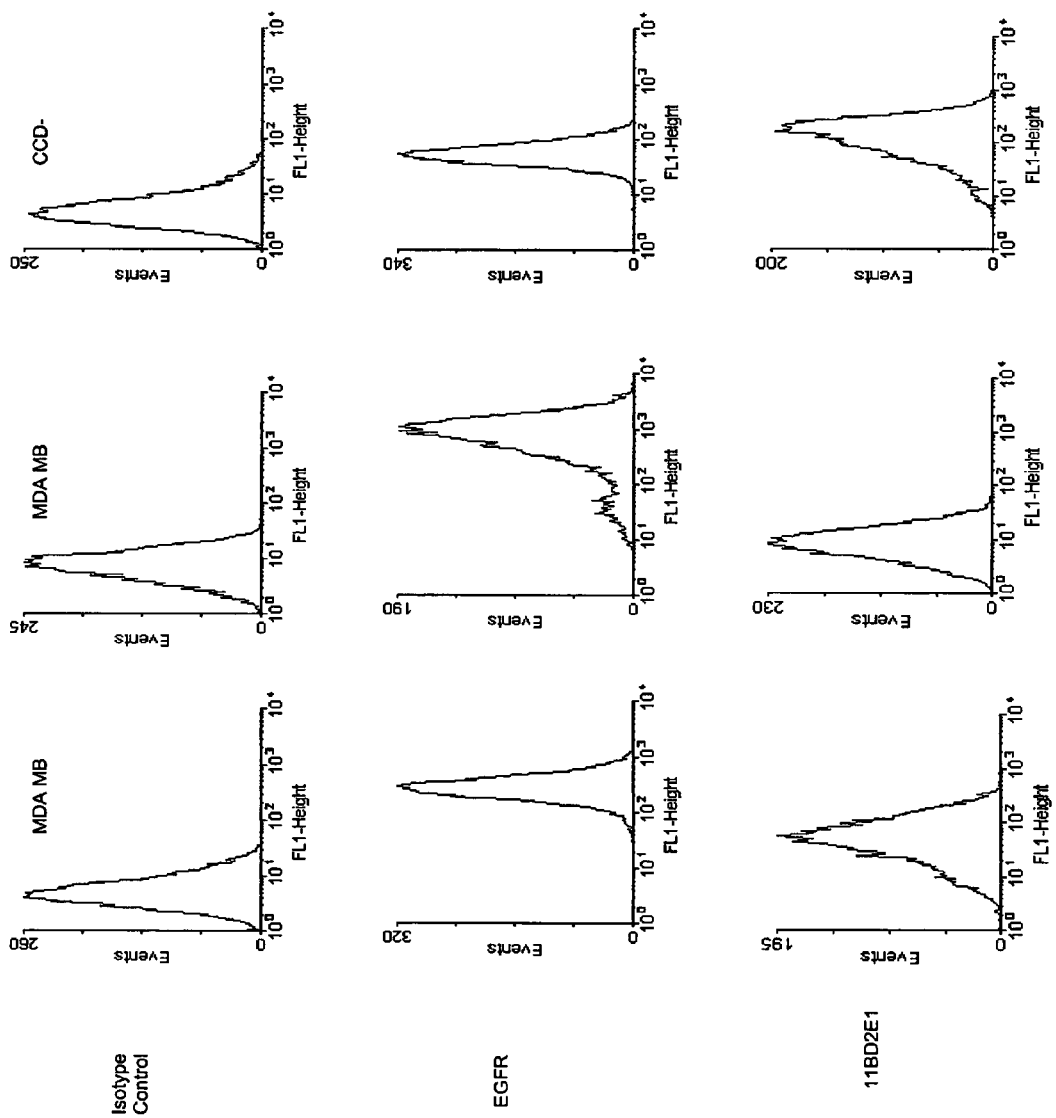
FIG. 3 includes representative FACS histograms of 11BD-2E11-2 antibodies, isotype control antibodies for both antibodies, anti-EGFR antibodies directed against several cancer cell lines and non-cancer cells.

Representative histograms of 7BD-33-11A antibodies were compiled for FIG. 1, 1A245.6 antibodies were compiled for FIG. 2, 11BD-2E11-2 were compiled for FIG. 3 and evidence the binding characteristics, inclusive of illustrated bimodal peaks, in some cases. 11BD-2E11-2 displayed specific tumor binding to the breast tumor cell line MDA-MB-231. Both 7BD-33-11A and 1A245.6 displayed similar binding to cancer lines of breast (MDA-MB-231 and MCF-7), colon, lung, ovary, and prostate origin and differential binding to one of the breast cancer cell lines (MDA-MB-468). There was binding of all three antibodies to non-cancer cells, however that binding did not produce cytotoxicity. This was further evidence that binding was not necessarily predictive of the outcome of antibody ligation of its cognate antigen, and was a non-obvious finding. This suggested that (45% of control) at day 67 (p=0.08). This also demonstrated a lesser tumor burden with cytotoxic antibody treatment in comparison to a control antibody. There was also corresponding survival benefits (FIG. 6) from treatment with 7BD-33-11A, 1A245.6, and 11BD-2E11-2 cytotoxic antibodies. The control group treated with 3BD-27 antibody reached 100% mortality by day 74 post-implantation. In contrast, groups treated with 7BD-33-11A were disease free and 1A245.6 treated animal displayed 100% survival and the group treated with 11BD-2E11-2 had 24% survival.

In toto, cytotoxic antibody treatment produced a decreased tumor burden and increased survival in comparison to a control antibody in a well recognized model of human cancer disease suggesting pharmacologic and pharmaceutical benefits of these antibodies (7BD-33-11A, 1A245.6, 11BD-2E11-2) for therapy in other mammals, including man.

EXAMPLE 4

In Vivo Established Tumor Experiments:

Five to six week old, female SCID mice were implanted with 5 million MDA-MB-231 breast cancer cells in one hundred microliters injected subcutaneously in the scruff of the neck. Tumor growth was measured with calipers every week. When the majority of the cohort reached a tumor volume of 100 mm$^3$ (range 50–200 mm$^3$) at 34 days post implantation 8–10 mice were randomly assigned into each of three treatment groups. 7BD-33-11A, 1A245.6 test antibodies or 3BD-27 isotype control antibody (known not to bind MDA-MB-231 cells) were administered intrapertioneally with 15 mg/kg of antibodies at a volume of 150 microliters after dilution from the stock concentration with a diluent that contained 2.7 mM KCl, 1 mM KH$_2$PO$_4$, 137 mM NaCl, 20 mM Na$_2$HPO$_4$. The antibodies were then administered three times per week for 10 doses in total in the same fashion until day 56 post-implantation. Tumor growth was measured about every seventh day with calipers until day 59 post-implantation or until individual animals reached the Canadian Council for Animal Care (CCAC) end-points. Body weights of the animals were recorded for the duration of the study. At the end of the study all animals were euthanised according to CCAC guidelines.

Figure 4:
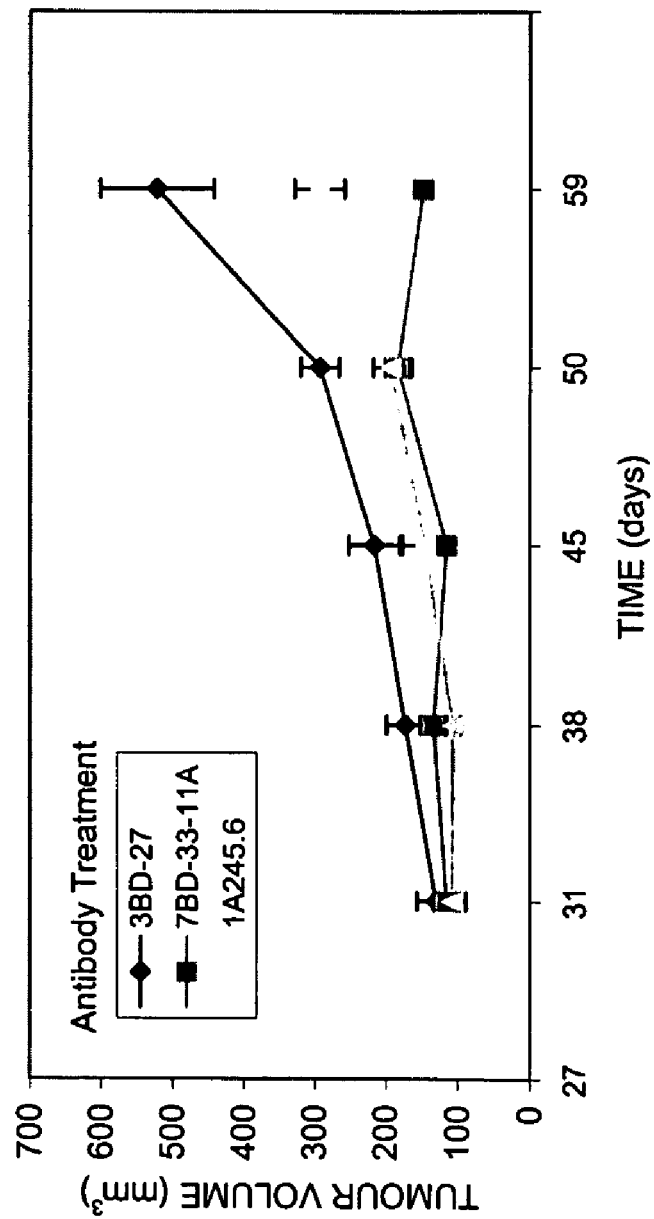
FIG. 4 is a graphical analysis of tumor volume over time with respect to particular antibody treatment.

There were no clinical signs of toxicity throughout the study. Body weight was measured at weekly intervals. There was no significant difference in weight for the groups treated with the isotype control and 7BD-33-11A, or 1A245.6 antibodies. As can be seen in FIG. 4, at day 59 post-implantation (2 days after the cessation of treatment), tumor volume of the group treated with 7BD-33-11A was 29.5% of the control group (p=0.0003). In this group, there was also a trend toward regression in mean tumor volume when the value for day 59 was compared to day 52 (p=0.25). Likewise, treatment with 1A245.6 antibody also significantly suppressed tumor growth and decreased tumor burdens. Animals with established tumors treated with this antibody had tumor volumes that were 56.3% of the isotype treated control group (p=0.017).

In toto, treatment with 7BD-33-11A or 1A245.6 antibodies significantly decreased the tumor burden of established tumors in comparison to a control antibody in a well recognized model of human cancer disease suggesting pharmacologic and pharmaceutical benefits of these antibodies for therapy in other mammals, including man.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. The isolated monoclonal antibody produced by the hybridoma deposited with the ATCC under Accession Number PTA-5643.

2. A humanized antibody of the isolated monoclonal antibody produced by the hybridoma deposited with the ATCC under Accession Number PTA-5643.

3. A chimeric antibody of the isolated monoclonal antibody produced by the hybridoma deposited with the ATCC under Accession Number PTA-5643.

4. A method for inducing cytotoxicity of cancerous cells in a tissue sample selected from a human breast or ovarian tumor comprising:
providing a tissue sample from said human breast or ovarian tumor;
providing the isolated monoclonal antibody produced by the hybridoma deposited with the ATCC as Accession Number PTA-5643 or an antigen binding fragment produced from said isolated monoclonal antibody; and
contacting said isolated monoclonal antibody or said antigen binding fragment with said tissue sample.

5. Antigen binding fragments of the isolated monoclonal antibody of claim 1.

6. Antigen binding fragments of the humanized antibody of claim 2.

7. Antigen binding fragments of the chimeric antibody of claim 3.

8. The isolated monoclonal antibody, humanized antibody, chimeric antibody or antigen binding fragments of any one of claims 1, 2, 3, 5, 6, or 7 conjugated with a member selected from the group consisting of cytotoxic moieties, enzymes, radioactive compounds, and hematogenous cells.

9. A method of treating a breast tumor in a mammal, comprising administering to said mammal the isolated monoclonal antibody produced by the hybridoma deposited with the ATCC as accession number PTA-5643 or an antigen binding fragment produced from said isolated monoclonal antibody in an amount effective to reduce said mammal's tumor burden.

10. The method of claim 9 wherein said isolated monoclonal antibody or said antigen binding fragment is conjugated to a cytotoxic moiety.

11. The method of claim 10 wherein said cytotoxic moiety is a radioactive isotope.

12. The method of claim 9 wherein said isolated monoclonal antibody activates complement.

13. The method of claim 9 wherein said isolated monoclonal antibody mediates antibody dependent cellular cytotoxicity.

14. The method of claim 9 wherein the antibody administered is a humanized antibody of the isolated monoclonal antibody produced by the hybridoma deposited with the ATCC under Accession Number PTA-5643.

15. The method of claim 9 wherein the antibody administered is a chimeric antibody of the isolated monoclonal antibody produced by the hybridoma deposited with the ATCC under Accession Number PTA-5643.

16. The isolated hybridoma deposited with the ATCC as Accession Number PTA-5643.

* * * * *